(12) United States Patent
Tsuruma (10) Patent No.: US 8,733,117 B2
(45) Date of Patent: May 27, 2014

(54) INCUBATOR

(75) Inventor: Ryuichi Tsuruma, Oizumi-machi (JP)

(73) Assignee: Panasonic Healthcare Co., Ltd., Toon-shi (JP)

( * ) Notice: Subject to any disclaimer, the term of this patent is extended or adjusted under 35 U.S.C. 154(b) by 889 days.

(21) Appl. No.: 12/894,950

(22) Filed: Sep. 30, 2010

(65) Prior Publication Data

US 2011/0126565 A1  Jun. 2, 2011

(30) Foreign Application Priority Data

Nov. 30, 2009 (JP) ................................. 2009-272540

(51) Int. Cl.
*F25B 41/00* (2006.01)
*F25B 29/00* (2006.01)
*B65H 3/28* (2006.01)

(52) U.S. Cl.
USPC .......... 62/208; 62/159; 165/48.1; 221/150 HC (58) Field of Classification Search
USPC .......... 62/159, 285, 259.1, 208; 165/59, 48.1; 221/150 HC, 150 R
See application file for complete search history.

(56) References Cited

U.S. PATENT DOCUMENTS

| | | |
|---|---|---|
| 5,033,803 A | 7/1991 | Katsuyoshi et al. |
| 5,773,287 A | 6/1998 | Binder |
| 2003/0085218 A1 | 5/2003 | Kauschke et al. |
| 2006/0063122 A1 | 3/2006 | Heeg et al. |
| 2006/0093514 A1 | 5/2006 | Dawes |

FOREIGN PATENT DOCUMENTS

| | | | |
|---|---|---|---|
| DE | 3630886 C1 | | 12/1987 |
| EP | 1634945 A1 | | 3/2006 |
| GB | 2 228 989 A | | 9/1990 |
| JP | 60-141279 A | | 7/1985 |
| JP | 04-152408 A | | 5/1992 |
| JP | 06347107 A | * | 12/1994 |
| JP | 07-075552 A | | 3/1995 |
| JP | 07-227270 A | | 8/1995 |
| JP | 10-234354 A | | 9/1998 |
| JP | 2001201229 A | * | 7/2001 |
| JP | 2003-047460 A | | 2/2003 |
| JP | 2006-217806 A | | 8/2006 |
| JP | 2008-014618 A | | 1/2008 |

OTHER PUBLICATIONS

European Search Report dated Apr. 13, 2011, issued in corresponding European Patent Application No. 10012299.3.
Japanese Office Action dated Jul. 16, 2013, issued in corresponding Japanese Patent Application No. 2009-272540.

* cited by examiner

*Primary Examiner* — Chen Wen Jiang
(74) *Attorney, Agent, or Firm* — Westerman, Hattori, Daniels & Adrian, LLP (57) ABSTRACT

An incubator includes: an enclosure including a culture chamber; a heater configured to heat the culture chamber; a refrigerator including an evaporator and a condenser, and configured to cool the culture chamber; a temperature sensor configured to measure the culture chamber temperature; a refrigerator control unit configured to cause the refrigerator to operate, when a measured temperature measured by the temperature sensor reaches a refrigerator-operation temperature, higher than the set temperature by a first temperature, and cause the refrigerator to stop operating, when the measured temperature reaches a refrigerator-operation stopping temperature, lower than the set temperature by a second temperature; a heater control unit configured to control the heater in such a manner that the measured temperature reaches the refrigerator-operation temperature, when operation of the refrigerator is stopped; and a drain mechanism configured to discharge dew condensation water generated through heat absorption by the evaporator out of the enclosure.

6 Claims, 8 Drawing Sheets

INCUBATOR

CROSS-REFERENCE TO RELATED APPLICATION

This application claims the benefit of priority to Japanese Patent Application No. 2009-272540, filed Nov. 30, 2009, of which full contents are incorporated herein by reference.

BACKGROUND OF THE INVENTION

1. Field of the Invention

The present invention relates to an incubator.

2. Description of the Related Art

As an incubator used for microbe culturing, food test, etc., an incubator with a heat-insulating and airtight enclosure including a heating means and a cooling means, and configured to control the temperature of a culture chamber to a temperature close to a set temperature by circulating air is known. For example, Japanese Laid-Open Patent Publication No. 2003-47460 discloses an incubator in which a blast fan is switched between rotating clockwise and counterclockwise, depending on a set temperature, to quickly circulate heated or cooled air, and to achieve uniform temperature distribution.

In this manner, by heating or cooling air and circulating it in the enclosure of a heat-insulating, airtight structure, the temperature of the culture chamber is controlled to a temperature close to the set temperature.

A moisture-containing object is placed in the culture chamber of the incubator in many cases, such as in a case of using a liquid culture media. In such a case, a higher culture chamber temperature results in evaporation of a greater amount of moisture, thus leading to an increase in the amount of water vapor in the culture chamber.

Therefore, when an open-air temperature is lower than the dew-point temperature of air in the culture chamber, dew condensation starts condensing on an area showing relatively low heat insulation of the inner surface of the enclosure. For example, dew condensation water is deposited on an observation window of a door, a packing sealing a gap between the enclosure body and the door, etc. If a set temperature drops because of manual setting or programmed automatic setting, dew condensation water may be deposited over a wide range on the inner surface of the enclosure.

This may lead to a situation where dew condensation water corrodes a metal portion of the enclosure or a waterdrop falls onto a culture media to cause contamination.

SUMMARY OF THE INVENTION

An incubator according to an aspect of the present invention, comprises: an enclosure including a culture chamber whose temperature is controlled depending on a set temperature; a heater configured to heat the culture chamber; a refrigerator including an evaporator configured to evaporate a cooling medium to allow the cooling medium to absorb heat from the culture chamber and a condenser configured to allow the cooling medium to release heat to condense the cooling medium, the refrigerator configured to cool the culture chamber; a temperature sensor configured to measure the temperature of the culture chamber; a refrigerator control unit configured to cause the refrigerator to operate, when a measured temperature measured by the temperature sensor reaches a temperature for refrigerator-operation, which is higher than the set temperature by a first temperature, and cause the refrigerator to stop operating, when the measured temperature reaches a temperature for stopping refrigerator-operation, which is lower than the set temperature by a second temperature; a heater control unit configured to control the heater in such a manner that the measured temperature reaches the temperature for refrigerator-operation, when operation of the refrigerator is stopped; and a drain mechanism configured to discharge dew condensation water generated through heat absorption by the evaporator out of the enclosure.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE INVENTION

At least the following details will become apparent from descriptions of this specification and of the accompanying drawings.

=Configuration of Incubator=

Figure 1:
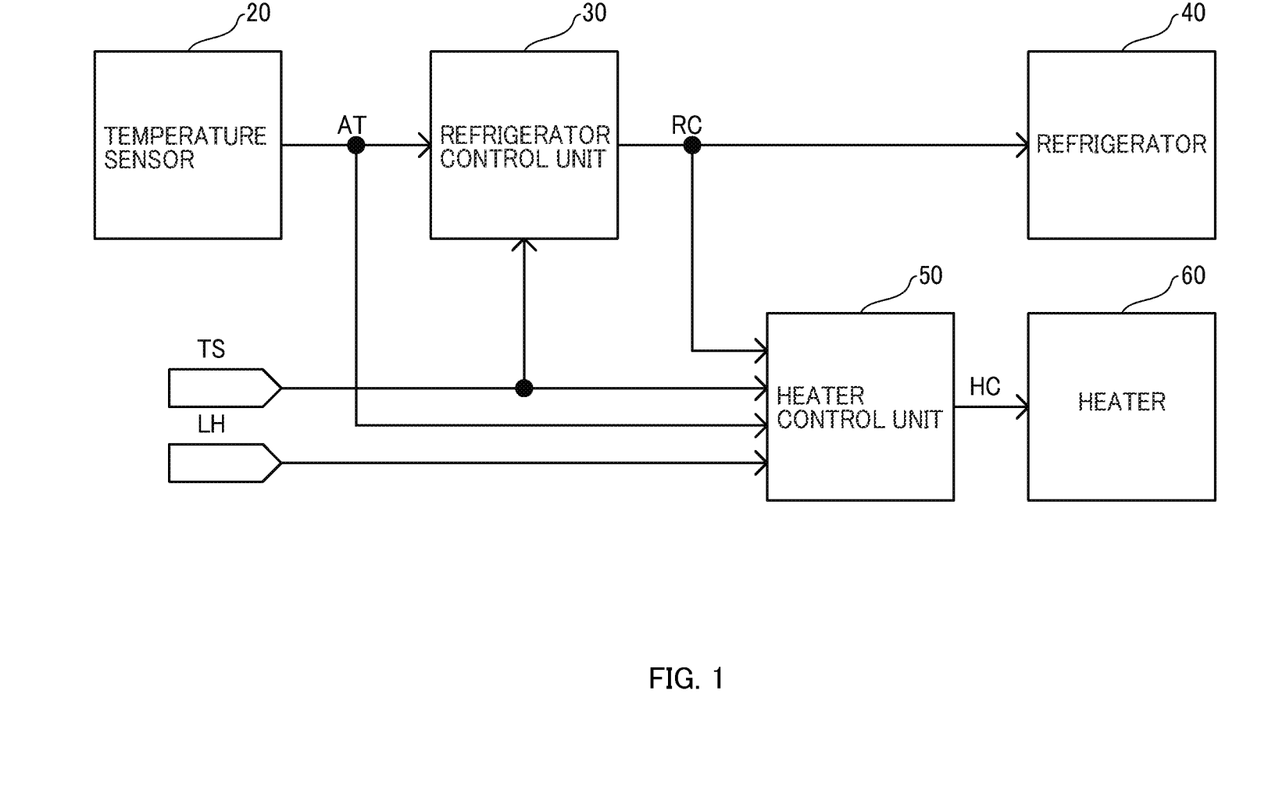
FIG. 1 is a block diagram of a configuration of a temperature control mechanism according to one embodiment of the present invention.
Figure 8:
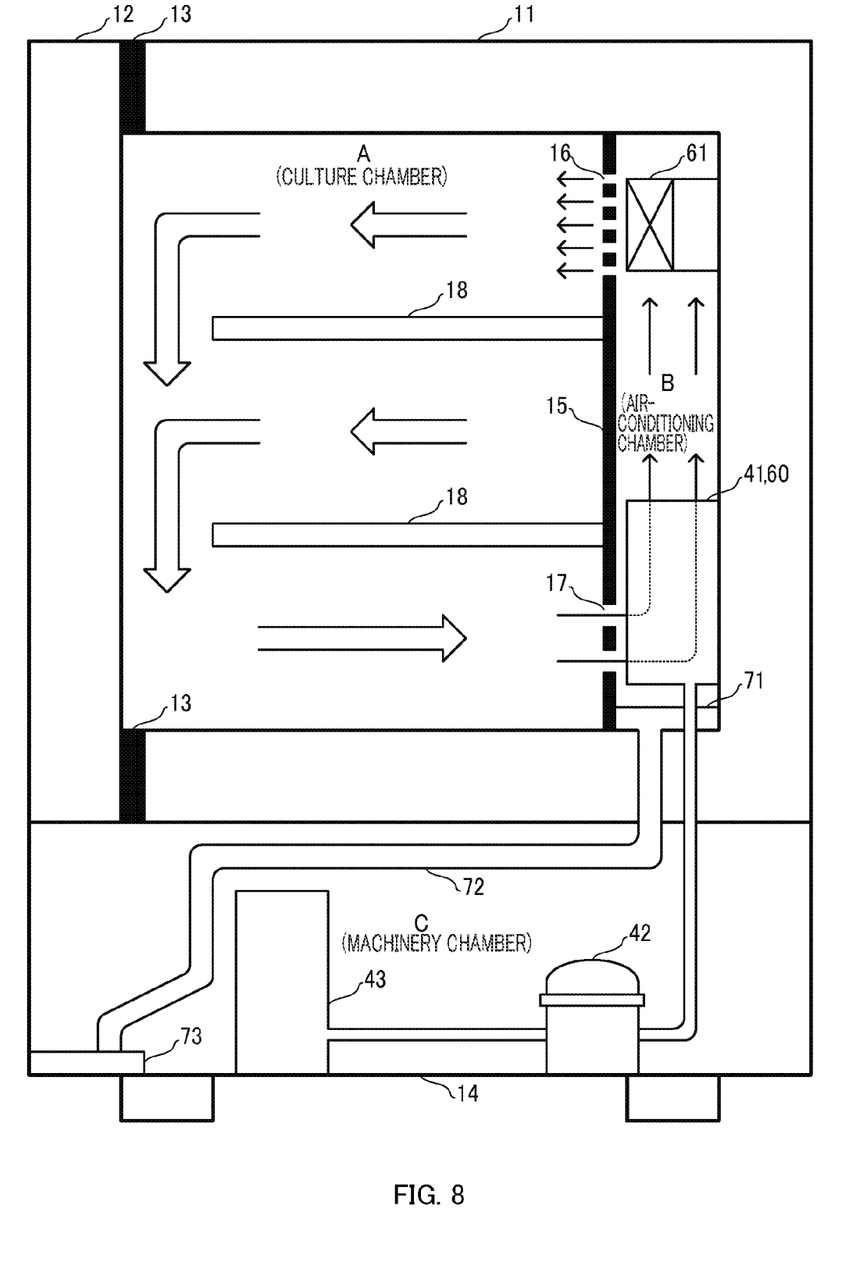
FIG. 8 is a perspective side view of a configuration of an incubator including the temperature control mechanism of one embodiment of the present invention.

A configuration of an incubator including a temperature control mechanism according to one embodiment of the present invention will now be described with reference to FIG. 8. FIG. 8 is a perspective side view of the interior of an enclosure and a pedestal of an incubator. The temperature control mechanism configured to control a heater and a refrigerator are shown in FIG. 1, and a detailed configuration of the temperature control mechanism will be described later.

In the incubator of FIG. 8, the enclosure composed of an enclosure body 11, a door 12, and a packing 13 is partitioned by a partition panel 15 into a culture chamber A and an air-conditioning chamber B. The pedestal 14 bearing the enclosure placed thereon has a machinery chamber C. The culture chamber A has shelves 18, the air-conditioning chamber B has an evaporator 41, a heater 60, a blower 61, and a dew-receiving tray 71, and the machinery chamber C has a compressor 42, a condenser 43, a hose 72, and an evaporation tray 73.

The enclosure body 11 is fitted with the openable/closable door 12. As shown in FIG. 8, when the door 12 is closed, a gap between the enclosure body 11 and the door 12 is sealed with the packing 13, and the enclosure is airtight. In addition, the enclosure body 11 and the door 12 are made of a heat-insulating material, and the enclosure has heat insulating properties.

The partition panel 15 has blowout holes 16 on its upper part and suction holes 17 on its lower part. On the side of the partition panel 15 facing the culture chamber A, the shelves 18 for placing a culture media, etc., thereon is fitted properly.

The evaporator 41, the compressor 42, and the condenser 43, together with an expansion valve (not shown), make up the refrigerator. The evaporator 41 is disposed near the suction port 17 of the air-conditioning chamber B. The compressor 42 and the condenser 43 are disposed in the machinery chamber C. A cooling medium circulates through a cooling medium pipeline to pass through the compressor 42, the condenser 43, the expansion valve, the evaporator 41, and the compressor 42 . . . , in this order.

The heater 60 serves also as a defrost heater, and is configured integrally with the evaporator 41. The blower 61 is disposed near the blowout holes 16 of the air-conditioning chamber B.

The dew-receiving tray 71, the hose 72, and the evaporation tray 73 make up a drain mechanism. The dew-receiving tray 71 is disposed below the evaporator 41, and the evaporation tray 73 is disposed in the mechanical chamber C. The hose 72 whose one end is connected to the dew-receiving tray 71 penetrates the enclosure body 11 and further extends to the evaporation tray 73.

=Operation of Incubator=

An operation of the incubator of this embodiment will next be described. A detailed operation of the temperature control mechanism will be described later, and only the outline of its operation is described here. A gas in the enclosure may be a gas other than ordinary air, for example, a gas whose carbon dioxide concentration is controlled.

The heater 60 according to control by the temperature control mechanism heats a gas in the air-conditioning chamber B, and the blower 61 blows the heated gas out through the blowout holes 16 to heat the culture chamber A. As the gas is blown out through the blowout holes 16, a gas in the culture chamber A is sucked in through the suction holes 17 into the air-conditioning chamber B. These blowout and suction actions cause the gas to circulate through the culture chamber A and the air-conditioning chamber B, as shown by arrows in FIG. 8, and thus uniform temperature distribution can be realized. In FIG. 8, the shelf 18 has a gas-permeable structure that allows the gas to circulate through the entire area of the culture chamber A.

The compressor 42, according to control by the temperature control mechanism, compresses the gaseous cooling medium in the cooling medium pipeline into the high-pressure gaseous cooling medium. The condenser 43 then allows the high-pressure gaseous cooling medium to release heat to condense the cooling medium into the liquid cooling medium. Further, the evaporator 41 evaporates the liquid cooling medium, which has been decompressed by the expansion valve and has a lower boiling point, to absorb heat from the gas sucked in through the suction holes 17. By repeating this cycle, the refrigerator cools the gas in the air-conditioning chamber B, and the blower 61 blows the cooled gas out through the blowout holes 16 to cool the culture chamber A.

In this manner, the incubator of this embodiment heats and/or cools a gas sucked through the suction holes 17 and blows the gas out through the blowout holes 16 to control the temperature of the culture chamber A.

When a water vapor-containing gas is sucked in through the suction holes 17 and is cooled by the refrigerator, there is a case where dew condensation occurs to result in the deposition of dew condensation water on the evaporator 41. The dew-receiving tray 71 receives dew condensation water deposited on the evaporator 41 to cause the dew condensation water to be discharged through the hose 72. Further, the evaporation tray 73 receives dew condensation water from the hose 72 to evaporate the dew condensation water with a heater, etc. (not shown). In this manner, a drain mechanism discharges dew condensation water generated through heat absorption by the evaporator 41 out of the enclosure to cause the dew condensation water to evaporate.

=Configuration of Temperature Control Mechanism=

A configuration of the temperature control mechanism of this embodiment will hereinafter be described with reference to FIG. 1.

The temperature control mechanism shown in FIG. 1 is the mechanism configured to control the heater 60 and the refrigerator 40, and is made including a temperature sensor 20, a refrigerator control unit 30, and a heater control unit 50.

The refrigerator control unit 30 receives input of a set temperature TS and a measured temperature AT output from the temperature sensor 20. A refrigerator control signal RC output from the refrigerator control unit 30 is input to the refrigerator 40.

The heater control unit 50 receives input of a selection signal LH and the refrigerator control signal RC, in addition to input of the set temperature TS and the measured temperature AT. A heater control signal HC output from the heater control unit 50 is input to the heater 60.

=Operation of Temperature Control Mechanism=

An operation of the temperature control mechanism of this embodiment will then be described with reference to FIGS. 2 and 3.

The incubator of this embodiment includes a control panel (not shown) set on the enclosure body 11 or the door 12. An operator operates a button or a switch on the control panel to set the set temperature TS. In the same manner, the operator makes a selection in determining whether to render effective or ineffective a low-humidity mode, which will be described later. When the low-humidity mode is rendered effective, the selection signal LH goes high. The set temperature TS is altered by manual setting by the operator, and may be altered according to a preset program.

The temperature sensor 20 measures the temperature of the culture chamber A to output the measured temperature AT, and the measured temperature AT is input together with the set temperature TS to the refrigerator control unit 30 and to the heater control unit 50. The refrigerator control unit 30 and the heater control unit 50 then control the refrigerator 40 and the heater 60, respectively, to maintain the measured temperature AT close to the set temperature TS.

Figure 2:
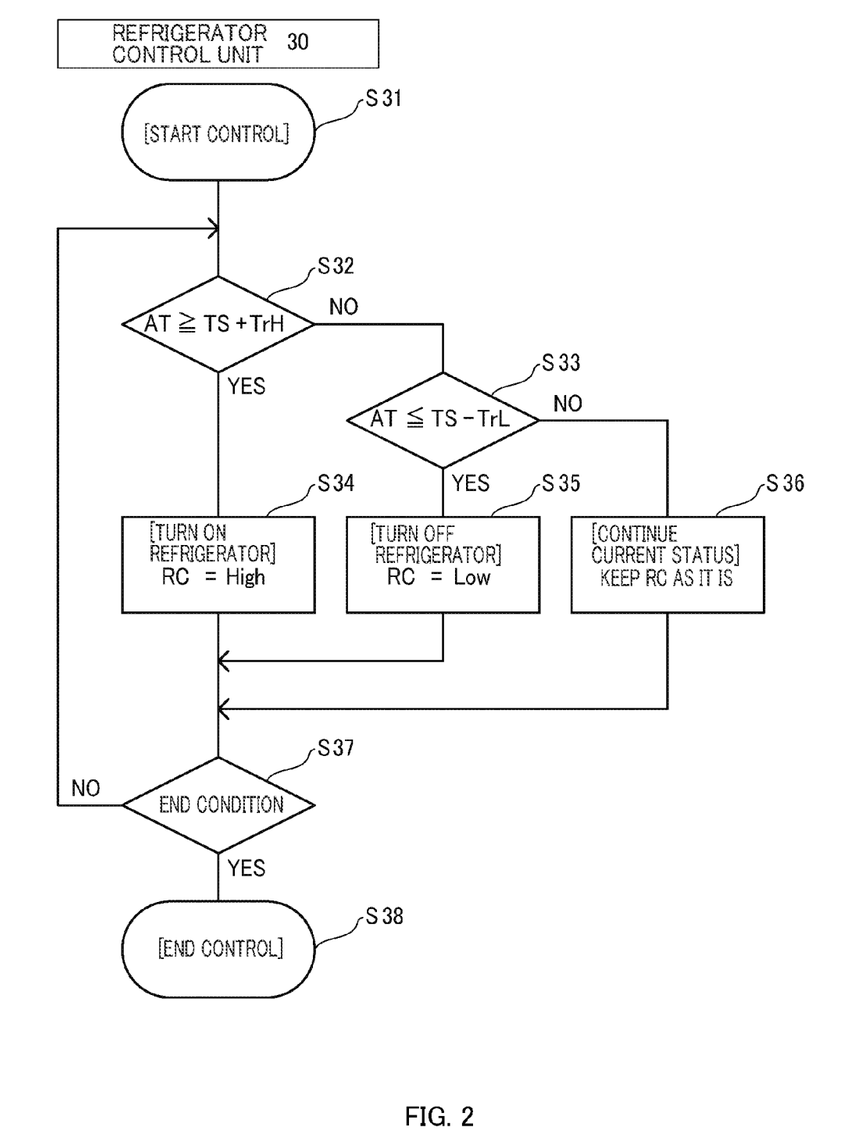
FIG. 2 is a flowchart for explaining an operation of a refrigerator control unit 30.

FIG. 2 shows an operation of the refrigerator control unit 30.

When starting control over the refrigerator 40 (S31), the refrigerator control unit 30 first compares the measured temperature AT with a temperature for refrigerator-operation (TS+TrH) higher than the setting temperature TS by a temperature TrH (first temperature) (S32). When the measured temperature AT is lower than the temperature for refrigerator-operation at S32 (S32: NO), the measured temperature AT is compared with a temperature for stopping refrigerator-operation (TS−TrL) lower than the setting temperature TS by a temperature TrL (second temperature) (S33).

When the result of comparison at S32 and S33 indicates that the measured temperature AT is equal to or higher than the temperature for refrigerator-operation (S32: YES), the refrigerator control unit 30 sets the refrigerator control signal RC high to operate the refrigerator 40 (S34). When the measured temperature AT is equal to or lower than the temperature for stopping refrigerator-operation (S33: YES), the refrigerator control unit 30 sets the refrigerator control signal RC low to stop the operation of the refrigerator 40 (S35). When the measured temperature AT is lower than the temperature for refrigerator-operation and is higher than the temperature for stopping refrigerator-operation (S33: NO), the refrigerator control unit 30 keeps the refrigerator control signal RC at the present level to cause the refrigerator 40 to continue the operation it has been carrying out previously (S36).

Subsequently, the refrigerator control unit 30 determines whether or not a temperature control end condition, such as manual stoppage by the operator and end of the program, is satisfied (S37). Until the end condition is satisfied (S37: NO), the above control over the refrigerator 40 is repeated. When the end condition is satisfied (S37: YES), the control over the refrigerator 40 is ended (S38).

In this manner, the refrigerator control unit 30 carries out control having hysteretic characteristics by causing the refrigerator 40 to operate when the measured temperature AT reaches the temperature for refrigerator-operation and causing the operation of the refrigerator 40 to stop when the measured temperature AT reaches the temperature for stopping refrigerator-operation.

Figure 3:
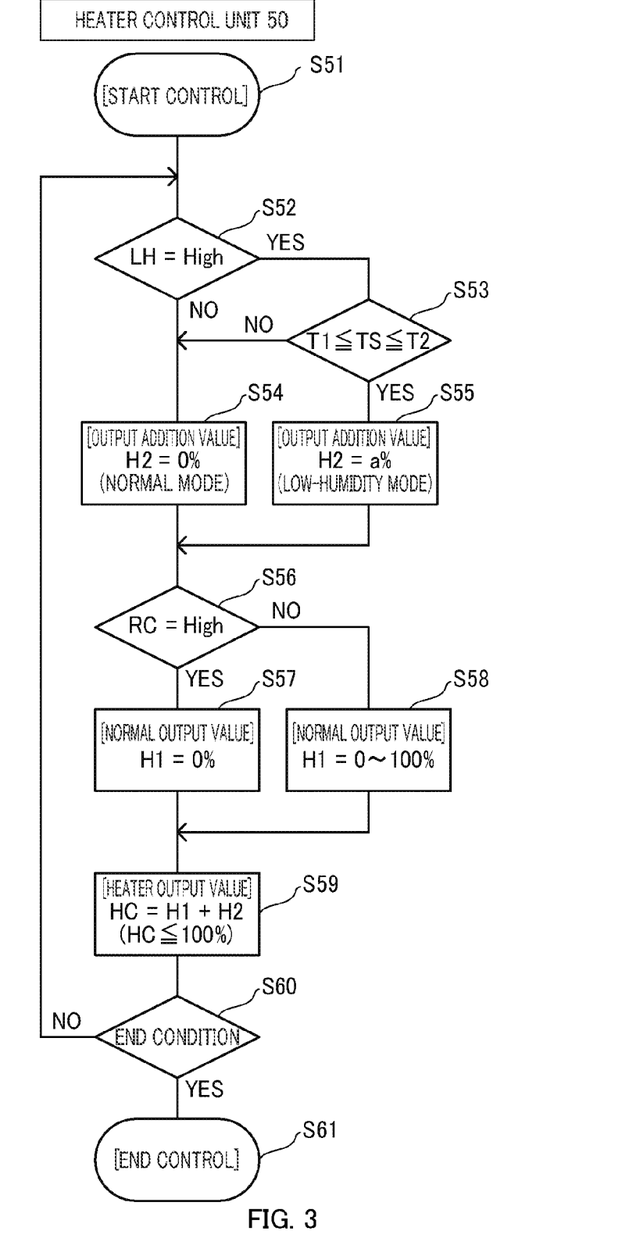
FIG. 3 is a flowchart for explaining an operation of a heater control unit 50.

FIG. 3 shows an operation of the heater control unit 50.

When starting control over the heater 60 (S51), in accordance with the selection signal LH and the setting signal TS, the heater control unit 50 first determines to which of a normal mode (first mode) and a low-humidity mode (second mode) a control mode is to be set (S52 and S53).

When the result of determination at S52 and S53 indicates that the selection signal LH is high and that the set temperature TS is within a low-humidity control range ranging from a temperature T1 or higher to a temperature T2 or lower (S52: YES and S53: YES), the heater control unit 50 controls the heater 60 in the low-humidity mode. In the low-humidity mode, an output addition value H2, which will be described later, is set to a % (0<a<100) (S55).

When the selection signal LH is low (S52: NO) or the set temperature TS is not within the low-humidity control range (S53: NO), the heater control unit 50 controls the heater 60 in the normal mode. In the normal mode, the output addition value H2 is set to 0% (0<a<100) (S54).

The heater control unit 50 then calculates a normal output value H1 that is an output value from the heater 60 in the normal mode, in accordance with the refrigerator control signal RC (S56). The normal output value H1 is calculated based on PID control in such a manner that the measured temperature AT matches the set temperature TS. When the refrigerator control signal RC is low (556: NO), the normal output value H1 is determined to be 0% or 100% (S58). When the refrigerator control signal RC is high (556: YES), the normal output value H1 is always determined to be 0% (S57).

The heater control unit 50 then outputs a heater output value HC given by adding the output addition value H2 to the normal output value H1 (S59). The heater 60 generates heat in accordance with the heater output value HC, and the heater 60 generates the maximum amount of heat when the heater output value HC is 100% and turns off when the heater output value HC is 0%. Even if the sum of the normal output value H1 and the output addition value H2 exceeds 100%, the heater output value HC is limited substantially to be equal to or less than 100%.

The heater control unit 50 then determines whether or not the temperature control end condition is satisfied (S60). The heater control unit 50 repeats the above control over the heater 60 until the end condition is satisfied (S60: NO), and when the end condition is satisfied (S60: YES), ends the control over the heater 60 (S61).

In this manner, the heater control unit 50 outputs the sum of the normal output value H1 calculated in accordance with the refrigerator control signal RC and the output addition value H2 set in accordance with the control mode, as the heater output value HC. The heater 60 then heats a gas in the air-conditioning chamber B by applying an amount of heat generated in accordance with the heater output value HC.

=Specific Example of Operation of Temperature Control Mechanism=

A specific example of an operation of the temperature control mechanism will be described appropriately referring to FIGS. 4 to 7.

Figure 4:
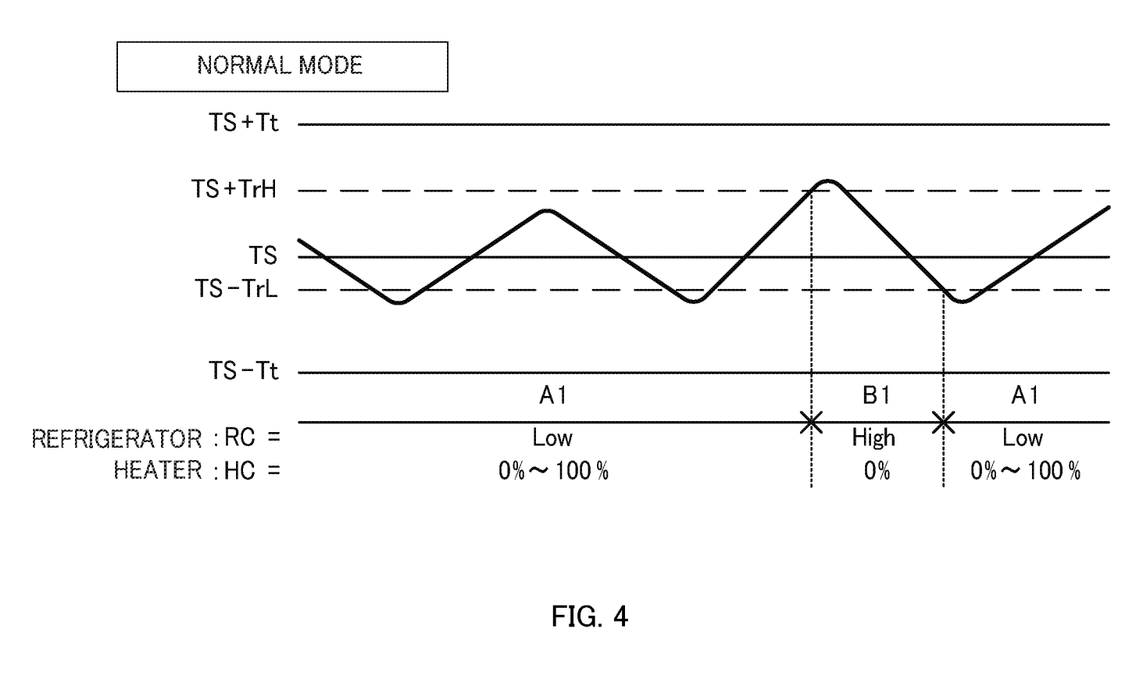
FIG. 4 shows an example of a temperature change in a culture chamber A in a normal mode.

An operation of the temperature control mechanism in the normal mode will first be described. FIG. 4 shows an example of a temperature change in the culture chamber A in the normal mode.

As described above, the refrigerator control unit 30 causes the refrigerator 40 to operate when the measured temperature AT reaches the temperature for refrigerator-operation and stops the operation of the refrigerator 40 when the measured temperature AT reaches the temperature for stopping refrigerator-operation. As a result, in a period during which the measured temperature AT does not reach the temperature for refrigerator-operation, the refrigerator 40 does not operate, and the temperature control mechanism controls only the heater 60 through the heater control signal HC output from the heater control unit 50.

In the normal mode, the output addition value H2 is set to 0%, as described above. This makes the heater output value HC equal to the normal output value H1. Further the normal output value H1 is calculated based on PID control in such a manner that the measured temperature AT matches the set temperature TS.

As a result, when the measured temperature AT is lower than the set temperature TS, the amount of heat generation from the heater 60 increases, and the temperature of the culture chamber A increases. When the measured temperature AT is higher than the set temperature TS, the amount of heat generation from the heater 60 decreases and the temperature of the culture chamber A is decreases. In a period A1 of FIG. 4, the temperature of the culture chamber A is controlled to a temperature close to the set temperature TS through control over the heater 60 only.

For example, when an open-air temperature (a temperature of a room in which the incubator is placed) is higher than the set temperature TS, the temperature of the culture chamber A does not drop even when the heater 60 is turned off by determining the heater output value HC to be 0%, and there are cases where the measured temperature AT reaches the temperature for refrigerator-operation. For example, even when the set temperature TS is altered to a low temperature by manual setting or a program, the measured temperature AT may reach the temperature for refrigerator-operation.

In these cases, since the measured temperature AT is sufficiently higher than the set temperature TS, the normal output value H1 calculated based on PID control is usually determined to be 0%. Even if the normal output value H1 is not determined to be 0%, the normal output value H1 usually turns out to be 0% as a result of the refrigerator control signal RC going high. As a result, when the measured temperature AT reaches the temperature for refrigerator-operation, the heater 60 turns off and the temperature control mechanism operates only the refrigerator 40 through the high refrigerator control signal RC.

Hence in a period B1 of FIG. 4, the temperature of the culture chamber A drops through the operation of only the refrigerator 40. When the temperature of the culture chamber A drops and the measured temperature AT reaches the temperature for stopping refrigerator-operation, the temperature control mechanism stops the operation of the refrigerator 40 to control only the heater 60 again.

In this manner, in the normal mode, the temperature control mechanism controls the heater 60, based on the normal output value H1 (first control value) calculated based on PID control, in such a manner that the measured temperature AT matches the set temperature TS. When the measured temperature AT reaches the temperature for refrigerator-operation, the temperature control mechanism causes only the refrigerator 40 to operate to lower the temperature of the culture chamber A. By controlling the refrigerator 40 and the heater 60 in this manner, the temperature of the culture chamber A is controlled to be within an allowable temperature range (TS−Tt to TS+Tt) close to the set temperature TS.

Figure 5:
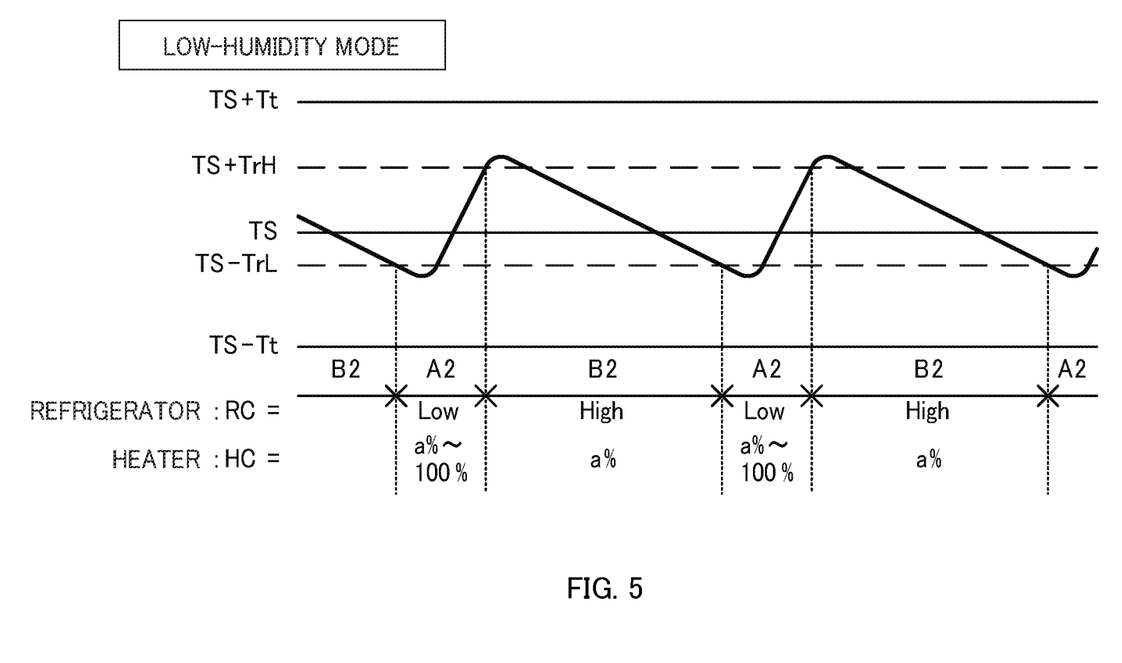
FIG. 5 shows an example of a temperature change in the culture chamber A in a low-humidity mode.

An operation of the temperature control mechanism in the low-humidity mode will next be described. FIG. 5 shows an example of a temperature change in the culture chamber A in the low-humidity mode.

In the low-humidity mode, the refrigerator control unit 30 controls the refrigerator 40 in the same manner as in the normal mode. In the low-humidity mode, because the output addition value H2 is set to a % (0<a<100), as described above, the heater output value HC is determined to be the value obtained by adding a % to the normal output value H1. This value of a % is set within a range such that the temperature of the culture chamber A drops when the refrigerator 40 is operating, and the measured temperature AT reaches the temperature for refrigerator-operation when the operation of the refrigerator 40 is stopped.

Hence the heater control unit 50 controls the heater 60 to cause it to generate heat greater than heat generated in the normal mode. As a result, in a period during which the refrigerator 40 stops its operation, the temperature of the culture chamber A rises faster than in the normal mode to cause the measured temperature AT to reach the temperature for refrigerator-operation, as shown in a period A2 of FIG. 5.

In this embodiment, the heater output value HC is limited substantially to be equal to or less than 100%, as described above. Therefore, when the sum of H1 and the value of a exceeds 100%, the amount of heat generation in the low-humidity mode becomes equal to the amount of heat generation in the normal mode. The amount of heat generation from the heater 60 in the case of the heater output value HC being 100%, however, may not be determined to be the maximum, in which case the heater 60 may be allowed to generate heat in response to the heater output value HC exceeding 100%.

When the measured temperature AT reaches the temperature for refrigerator-operation, the refrigerator 40 operates, and on the contrary the heater 60 generates heat as an amount of heat in the case of the heater output value HC being a %. As a result, as shown in a period B2 of FIG. 5, the temperature of the culture chamber A drops more slowly than in the normal mode.

In this manner, in the low-humidity mode, the temperature control mechanism controls the heater 60 based on the value (second control value) given by adding a % (prescribed addition value) to the normal output value H1 (first control value) calculated based on PID control, and controls the refrigerator 40 in the same manner as in the normal mode. Controlling the refrigerator 40 and the heater 60 in this manner causes the refrigerator 40 to operate more frequently than in the normal mode, which results in the deposition of dew condensation water on the evaporator 41.

As described above, dew condensation water deposited on the evaporator 41 is discharged out of the enclosure and evaporates at the evaporation tray 73. As a result, in the low-humidity mode, the amount of water vapor in the culture chamber A decreases to become less than the amount of water vapor in the normal mode. This suppresses deposition of dew condensation water on the inner surface of the enclosure.

Figure 6:
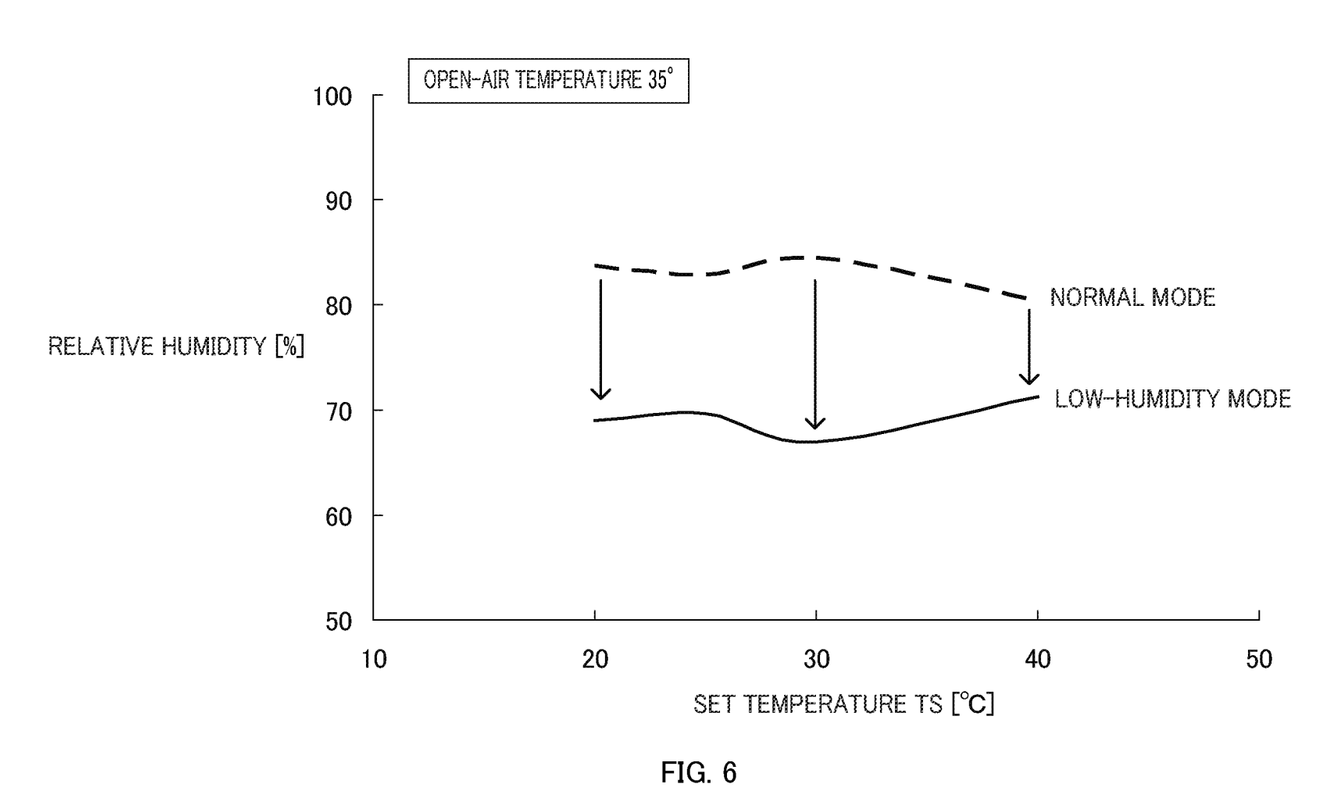
FIG. 6 shows an example of the relation between a set temperature and a relative humidity in the normal mode and in the low-humidity mode under an open-air temperature of 35° C.
Figure 7:
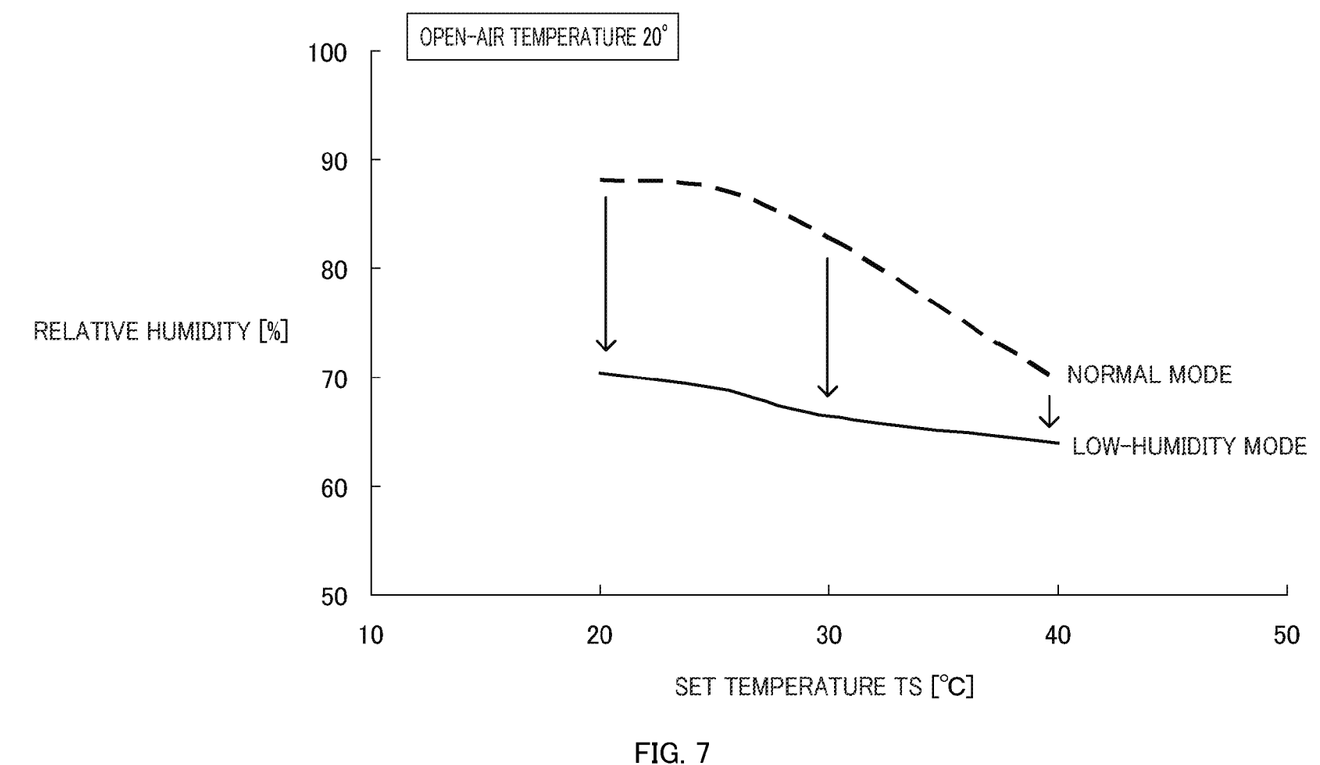
FIG. 7 shows an example of the relation between a set temperature and a relative humidity in the normal mode and in the low-humidity mode under an open-air temperature of 20° C.

FIGS. 6 and 7 show examples of the relation between a set temperature and a relative humidity in the cases of open-air temperatures of 35° C. and 20° C., with the low-humidity control range of 20° C. or higher to 40° C. or lower. FIGS. 6 and 7 clearly demonstrate that the relative humidity in the low-humidity mode is lower than the relative humidity in the normal mode in both examples. This means that the amount of water vapor in the culture chamber A can be reduced in the low-humidity mode than compared to in the normal mode.

As described above, with the incubator including the temperature control mechanism, when the operation of the refrigerator 40 is stopped, the heater 60 is controlled to cause the measured temperature AT to reach the temperature for refrigerator-operation, thus facilitating deposition of dew condensation water on the evaporator 41 while discharging the dew condensation water out of the enclosure. This reduces the amount of water vapor in the culture chamber A, and thus can suppress deposition of dew condensation water on the inner surface of the enclosure.

While the heater 60 is controlled in such a manner that the measured temperature AT matches the set temperature TS in the normal mode, the heater 60 is controlled to increase the amount of heat generation in the low-humidity mode. Therefore, in the low-humidity mode, the refrigerator 40 is operated more frequently than in the normal mode to facilitate deposition of dew condensation water on the evaporator 41.

In the low-humidity mode, the value obtained by adding a % to the normal output value H1 calculated based on PID control is determined to be the heater output value HC to cause the measured temperature AT to reach the temperature for refrigerator-operation faster than in the normal mode. This causes the refrigerator 40 to operate more frequently than in the normal mode.

The normal mode and the low-humidity mode are switched between each other in accordance with not only the selection signal LH but also the set temperature TS. Therefore, when the set temperature TS is not within the low-humidity control range, the control mode can be prevented from being switched to the low-humidity mode.

The blower 61 is disposed near the blowout holes 16 on the upper part of the partition panel 15, and the heater 60 and the evaporator 41 are disposed near the suction holes 17 on the lower part of the partition panel 15. This causes a gas to circulate in the culture chamber A and the air-conditioning chamber B, makes temperature distribution uniform and causes dew condensation water depositing on the evaporator 41 to be quickly discharged out of the enclosure.

Dew condensation water, which is discharged from the enclosure to the outside, is to be evaporated at the evaporation tray 73. This enables efficient discharge of dew condensation water deposited on the evaporator 41.

While the refrigerator 40 is described as the compression refrigerator including the compressor 42 in the embodiment, the refrigerator 40 is not limited to this type. The refrigerator 40, for example, may be an absorption refrigerator not including a compressor, in which case the evaporator and the condenser are disposed in the same manner as in FIG. 8.

While PID control is adopted as a method of controlling the heater 60 in such a manner that the measured temperature AT matches the set temperature TS in the embodiment, the method of control is not limited to this. Other methods of feedback control, such as P control and PI control, may be adopted as the method of controlling the heater 60. Feedback control and feedforward control may be used in combination.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. An incubator comprising:
   an enclosure including a culture chamber whose temperature is controlled depending on a set temperature;
   a heater configured to heat the culture chamber;
   a refrigerator including an evaporator configured to evaporate a cooling medium to allow the cooling medium to absorb heat from the culture chamber and a condenser configured to allow the cooling medium to release heat to condense the cooling medium, the refrigerator configured to cool the culture chamber;
   a temperature sensor configured to measure the temperature of the culture chamber;
   a refrigerator control unit configured to
      cause the refrigerator to operate, when a measured temperature measured by the temperature sensor reaches a temperature for refrigerator-operation, which is higher than the set temperature by a first temperature, and
      cause the refrigerator to stop operating, when the measured temperature reaches a temperature for stopping refrigerator-operation, which is lower than the set temperature by a second temperature;
   a heater control unit configured to control the heater in such a manner that the measured temperature reaches the temperature for refrigerator-operation, when operation of the refrigerator is stopped; and
   a drain mechanism configured to discharge dew condensation water generated through heat absorption by the evaporator out of the enclosure; and wherein
   the heater control unit switches between a first mode and a second mode in accordance with a selection signal, wherein
   the first mode is a mode where the heater is controlled in such a manner that the measured temperature matches the set temperature, and
   the second mode is a mode where the heater is controlled to generate heat greater in amount than heat in the first mode in such a manner that the measured temperature reaches the temperature for refrigerator-operation when operation of the refrigerator is stopped.

2. The incubator of claim 1, wherein
   the heater control unit inputs to the heater a first control value calculated based on PID control in the first mode, and inputs to the heater a second control value obtained by adding a predetermined addition value to the first control value in the second mode.

3. The incubator of claim 2, wherein
   the heater control unit switches between the first mode and the second mode in accordance with the selection signal and the set temperature.

4. The incubator of claim 1, wherein
   the heater control unit switches between the first mode and the second mode in accordance with the selection signal and the set temperature.

5. The incubator of claim 1, further comprising:
   a partition panel having a gas blowout hole and a gas suction hole on an upper part thereof and a lower part thereof, respectively, the partition panel partitioning an interior of the enclosure into the culture chamber and a space in which the heater and the evaporator are disposed; and
   a blower configured to blow a gas out through the blowout hole into the culture chamber, and suck a gas in through the suction hole from the culture chamber, wherein
   the heater heats a gas sucked in through the suction hole, and
   the evaporator allows the cooling medium to absorb heat from a gas sucked in through the suction hole.

6. The incubator of claim 1, wherein
   the drain mechanism includes
   a dew-receiving tray for receiving the dew condensation water deposited on the evaporator, and
   an evaporation tray for receiving the dew condensation water, which is discharged from the dew-receiving tray to an outside of the enclosure, to be evaporated.

* * * * *